(12) United States Patent
Kuranishi

(10) Patent No.: US 6,641,529 B2
(45) Date of Patent: Nov. 4, 2003

(54) ENDOSCOPE APPARATUS AND METHOD OF CONTROLLING SAME

(75) Inventor: Hideaki Kuranishi, Ashigarakami-gun (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 0 days.

(21) Appl. No.: 10/163,603

(22) Filed: Jun. 7, 2002

(65) Prior Publication Data
US 2002/0188176 A1 Dec. 12, 2002

(30) Foreign Application Priority Data
Jun. 8, 2001 (JP) ........................................ 2001-173737

(51) Int. Cl.$^7$ .............................................. A61B 1/045
(52) U.S. Cl. ........................ 600/160; 600/109; 600/178; 600/921; 348/68
(58) Field of Search ................................. 600/109, 160, 600/178, 921, 476, 477, 478; 348/65, 68, 69, 71, 76

(56) References Cited

U.S. PATENT DOCUMENTS

| 4,878,112 | A | * | 10/1989 | Ieoka .......................... 348/70 |
| 5,142,359 | A | * | 8/1992 | Yamamori .................... 348/70 |
| 6,489,987 | B1 | * | 12/2002 | Higuchi et al. ................ 348/65 |
| 6,518,998 | B1 | * | 2/2003 | Christoff et al. .......... 348/216.1 |
| 6,529,768 | B1 | * | 3/2003 | Hakamata .................... 600/476 |

FOREIGN PATENT DOCUMENTS

JP        10257250    *    9/1998

* cited by examiner

*Primary Examiner*—John P. Leubecker
(74) *Attorney, Agent, or Firm*—Sughrue Mion, PLLC

(57) ABSTRACT

A correction for dark current is performed in comparatively accurate fashion. To accomplish this, emissions of both ordinary light and excitation light are turned off when a changeover is made between a ordinary-light observation mode, in which internal tissue is imaged by illuminating it with ordinary light, and an excitation-light observation mode, in which internal tissue is imaged by illuminating it with excitation light. A dark-current correction is performed using data (dark-current data) obtained by imaging the internal tissue while no light is illuminating the internal tissue.

5 Claims, 6 Drawing Sheets

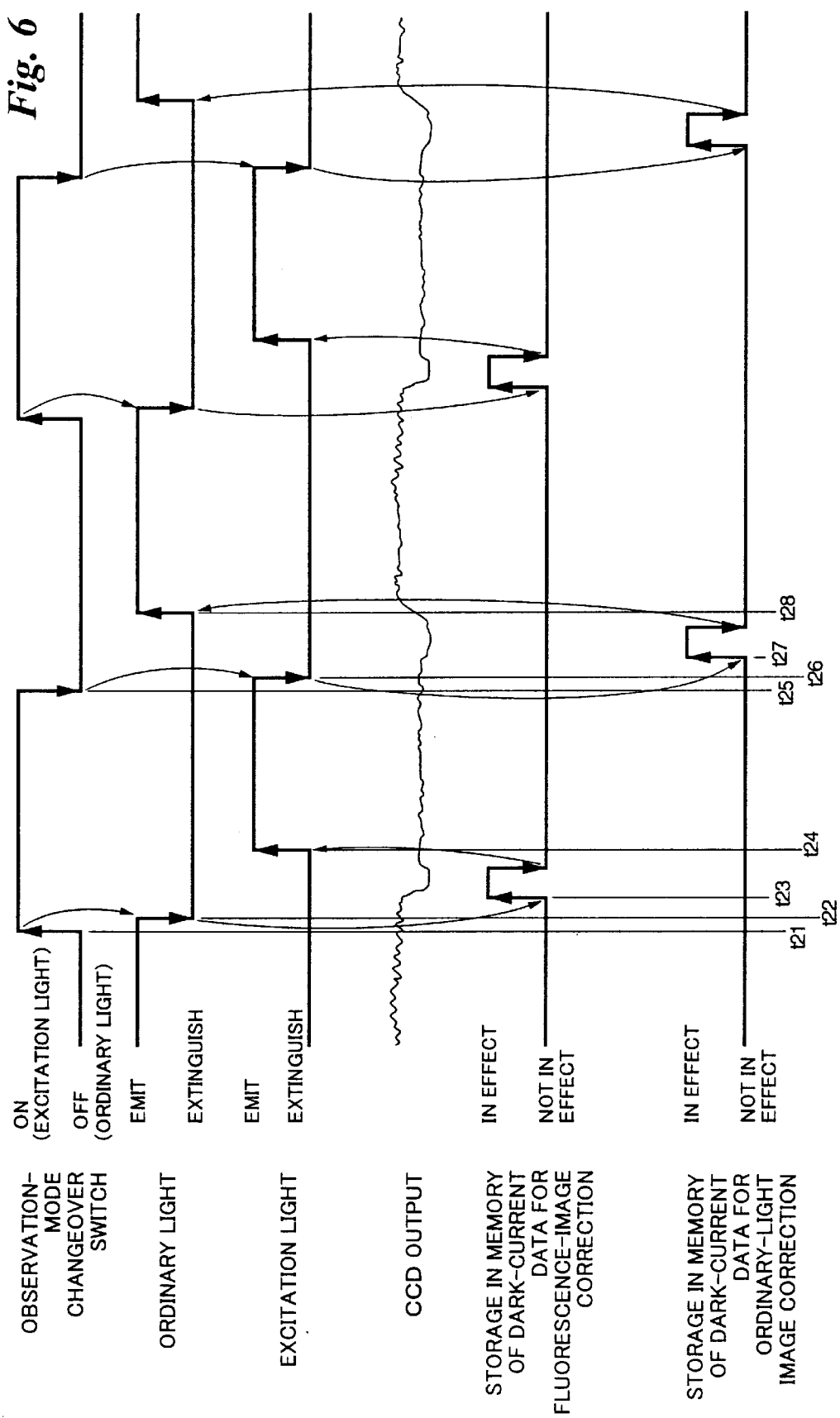

ENDOSCOPE APPARATUS AND METHOD OF CONTROLLING SAME

BACKGROUND OF THE INVENTION

1. Field of the Invention

This invention relates to an endoscope apparatus and to a method of controlling the operation thereof.

2. Description of the Related Art

An endoscope apparatus has an ordinary-light observation mode and a fluorescent observation mode. Until the tip of a fiber scope of the endoscope apparatus reaches the vicinity of internal tissue (an object of interest) deemed to be the affected area, the internal tissue is imaged while it is irradiated with white light in the ordinary-light observation mode. When the tip of the fiber scope reaches the vicinity of the internal tissue deemed to be the affected area, the internal tissue is irradiated with excitation light. The pigment of the internal tissue responds by emitting fluorescence, the image of the internal tissue is sensed by a solid-state electronic image sensing device, and image data representing the internal tissue is obtained. A diagnosis is made based upon the image of the internal tissue represented by the obtained image data.

A solid-state electronic image sensing device produces an output (dark current) even when light is not impinging upon it. For this reason the dark current is measured and a correction (dark-current correction) is applied to subtract the value of the dark current from the value of the output of the solid-state electronic image sensing device that prevails when light is incident upon the solid-state electronic image sensing device. The dark-current correction is carried out as follows:

In a first method, the solid-state electronic image sensing device is shielded from light and the dark current is measured before the fiber scope of the endoscope apparatus is inserted into the body of the patient. Data ascribable to the dark current is subtracted from image data obtained by sensing the internal tissue of the patient.

A problem, however, is that the dark current varies in dependence upon the temperature of the solid-state electronic image sensing device. An accurate dark-current correction cannot be made because there is a temperature difference between the temperature of the solid-state electronic image sensing device, which is located at the tip of the fiber scope, when it is inside the body of the patient and the temperature thereof when it is outside the body of the patient (the temperature inside the body of the patient is higher).

In a second method, the fiber scope of the endoscope apparatus is inserted into the body of the patient and data obtained from an optical black region of the solid-state electronic image sensing device at the tip of the fiber scope while the internal tissue is being illuminated is regarded as data indicative of the dark current. Data obtained from the optical black region is subtracted from the image data acquired by imaging the internal tissue.

Though the optical black area is shielded from light by a film of vacuum-deposited aluminum or the like, perfect shielding is difficult. Consequently, there are occasions where an accurate dark-current correction cannot be performed.

DISCLOSURE OF THE INVENTION

Accordingly, an object of the present invention is to perform a comparatively accurate dark-current correction in an endoscope apparatus.

According to the present invention, the foregoing object is attained by providing an endoscope apparatus comprising: a light source for emitting first light having a first wavelength characteristic in a first observation mode and emitting second light having a second wavelength characteristic in a second observation mode; an image sensing device for outputting image data representing an object of interest in an area illuminated by light emitted from the light source; a controller for controlling the light source so as to halt emission of light when there is a mode changeover between the first and second observation modes; and a correction device for correcting image data, which is output from the image sensing device and represents the image of the object of interest that was illuminated by at least one of the first light and second light, after the light emission is halted, using data output from the image sensing device when the emission of light from the light source is halted by the controller.

The present invention also provides a control method suited to the above-described endoscope apparatus. Specifically, the present invention provides a method of controlling an endoscope apparatus having a light source for emitting first light having a first wavelength characteristic in a first observation mode and emitting second light having a second wavelength characteristic in a second observation mode, and an image sensing device for outputting image data representing an object of interest in an area illuminated by light emitted from the light source, the method comprising the steps of: controlling the light source so as to halt emission of light when there is a mode changeover between the first and second observation modes; and correcting image data, which is output from the image sensing device and represents the image of the object of interest that was illuminated by at least one of the first light and second light, after the emission of light is halted, using data output from the image sensing device when the emission of light from the light source is halted.

In accordance with the present invention, the image sensing device is inserted into the body, first light having a first wavelength characteristic is emitted in a first observation mode and second light having a second wavelength characteristic is emitted in a second observation mode, thereby illuminating the object of interest (a patient's internal tissue). The emission of light from the light source is halted when a changeover is made between the first and second observation modes.

When the emission of light from the light source is halted, the image sensing device outputs data (dark-current data output from the solid-state electronic image sensing device owing to dark current). By using the data obtained when the light emission from the light source is halted, a correction (dark-current correction) is applied to image data (inclusive of image data obtained periodically by movie photography and image data obtained by still-picture photography) representing the image of the object of interest that was illuminated by at least one of the first and second light.

Thus, dark current is obtained from the solid-state electronic image sensing device when the device has been inserted into the body. Image data representing the image of the internal tissue that was obtained by sensing the image of the illuminated object of interest is corrected using the obtained dark current.

Since both the data representing the dark current and the image data to be corrected are obtained when the image sensing device is inside the body, there is little variation in temperature. This makes it possible to eliminate the effects of temperature fluctuation. Further, since illumination is halted when the dark current is obtained, a comparatively accurate dark current can be obtained. (Since the image sensing device is inside the body, the device is shielded from light almost perfectly when illumination is halted.) As a result, a comparatively accurate dark-current correction can be achieved.

It is preferred that the image data corrected by the correction device be image data of the object of interest illuminated by the light source immediately after halting of the light emission.

Since the dark-current correction is carried out using dark current obtained immediately prior to imaging of the object of interest illuminated by the first and second light, a more accurate correction can be applied.

The controller may control the light source so as to halt the emission of light every time there is a mode changeover between the first and second observation modes. In this case, the correction device would correct the image data, which is output from the image sensing device and represents the image of the object of interest that was illuminated by at least one of the first light and second light, immediately after the emission of light is halted every time the emission of light is halted, using image data output from the image sensing device and representing the image of the subject every time the emission of light from the light source is halted by the controller.

Thus, a correction can be applied using dark current obtained immediately before every changeover between the first and second observation modes.

By way of example, the first light of the light source is visible light and the second light is excitation light for obtaining a fluorescent image of internal tissue. The second light may be near infrared light.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

FIG. 6 is a time chart for when internal tissue is imaged using the endoscope apparatus of the second embodiment.

DESCRIPTION OF THE PREFERRED EMBODIMENTS

Preferred embodiments of the present invention will be described in detail with reference to the drawings.

Figure 1:
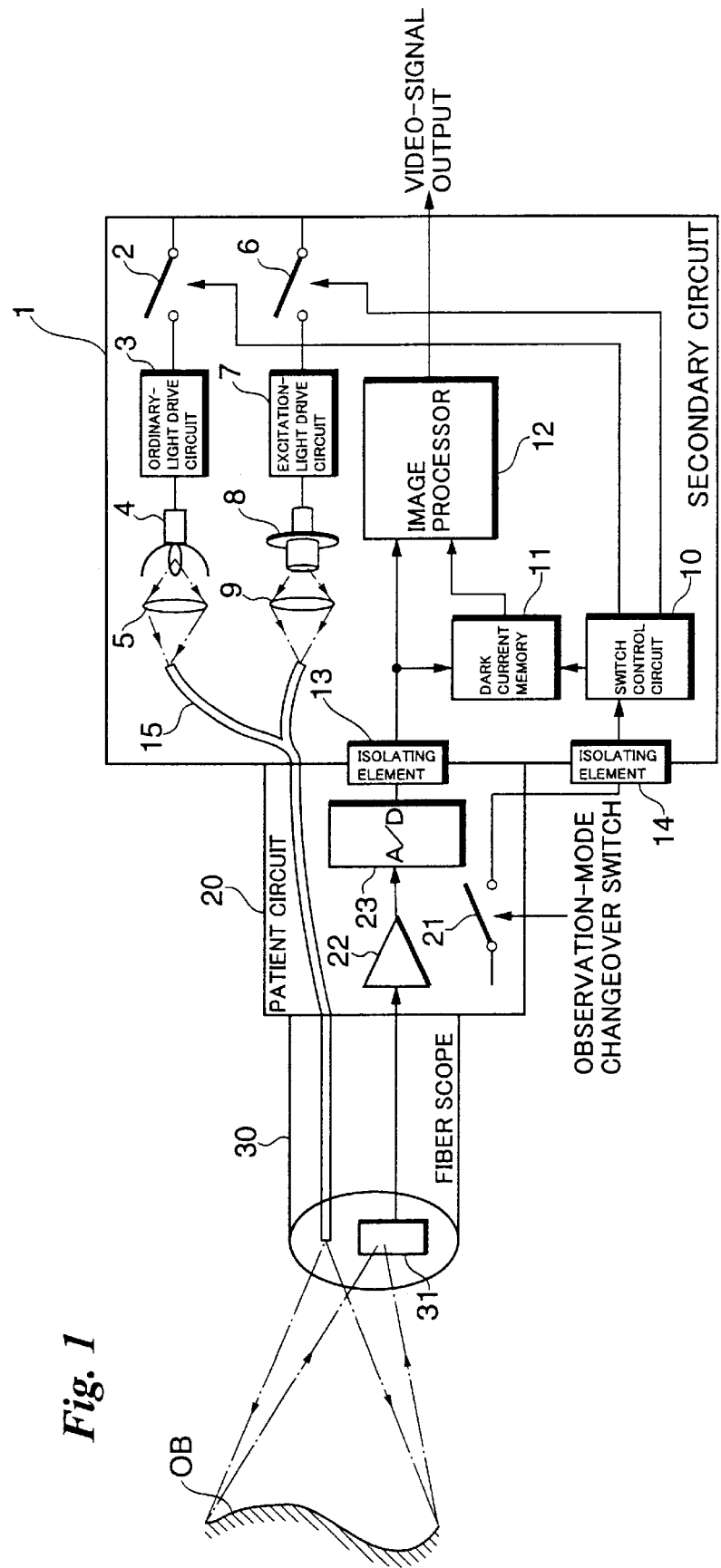
FIG. 1 is a block diagram illustrating the electrical structure of an endoscope apparatus according to a first embodiment of the present invention.

FIG. 1 is a block diagram illustrating the electrical structure of an endoscope apparatus according to a first embodiment of the present invention.

As shown in FIG. 1, the endoscope apparatus comprises a secondary circuit 1, a patient circuit (primary circuit) 20 and an elongated, flexible fiber scope 30. The secondary circuit 1 and patient circuit 20 are placed on a table or the like and is operated by a physician. When a patient lies down on a bed and the patient's stomach lining, for example, is to be imaged as internal tissue (the object of interest), the physician inserts the fiber scope 30 from the patient's mouth. The fiber scope 30 is passed through the esophagus until the tip of the fiber scope 30 reaches the interior of the stomach. As will be described later, the tip of the fiber scope 30 is provided with a CCD 31 for sensing the image of the stomach lining, which represents internal tissue OB.

The endoscope apparatus has two observation modes, namely an ordinary-light observation mode (first observation mode) and a fluorescent observation mode (second observation mode). The ordinary-light observation mode is for sensing the image of the internal tissue OB by illuminating it with white light. The fluorescent observation mode is for sensing the image of the internal tissue OB by illuminating it with excitation light.

The patient circuit 20 is provided with a observation-mode changeover switch 21, which is turned on and of by the physician operating the endoscope apparatus. The fluorescent observation mode is established by turning on the observation-mode changeover switch 21, and the ordinary-light observation mode is established by turning off the observation-mode changeover switch 21.

A signal indicating the on/off state of the observation-mode changeover switch 21 is input to a switch control circuit 10 of the secondary circuit 1 via an isolating element (photocoupler) 14. Switch circuits 2 and 6 included in the secondary circuit 1 are controlled by the switch control circuit 10 in such a manner that the switch circuit 6 is turned on when the observation-mode changeover switch 21 is turned on and the switch circuit 2 is turned on when the observation-mode changeover switch 21 is turned off.

When the switch circuit 2 is turned on, an ordinary light source (white-light source) 4 is caused to emit white light by a drive circuit 3 for ordinary light. The white light is introduced to the rear end face (the face on the side of the secondary circuit 1) of a light guide 15, which is disposed within the patient circuit 20 and fiber scope 30, by a condensing lens 5.

When the switch circuit 6 is turned on, an excitation light source 8 is caused to emit excitation light, which has a wavelength characteristic in the excitation-wavelength region of the internal tissue, by a driving circuit 7 for excitation light. (It may be so arranged that the excitation light source 8 emits near infrared light.) The excitation light is introduced to the rear end face of the light guide 15 by a condensing lens 9.

The illuminating light (white light or excitation light) propagates through the interior of the light guide 15 and emerges from the front end of the light guide 15. An illumination lens (not shown) is placed in front of the front end face of the light guide 15. The light emitted from the light guide 15 illuminates the internal tissue OB owing to the illumination lens.

Light reflected from the internal tissue OB is condensed by an objective lens (not shown). (When excitation light emerges from the light guide 15, then the internal tissue OB produces self-fluorescence as the reflected light.) As a result, an image representing the internal tissue OB is formed on the photoreceptor surface of a CCD 31. A video signal representing the image of the internal tissue OB is output from the CCD 31, and the signal is input to an amplifier 22 provided in the patient circuit 20.

The amplifier 22 amplifies the video signal, and the amplified signal is converted to digital image data in an analog/digital converter 23. The digital image data is input to an image processor 12 in the secondary circuit 1 via an isolating element 13.

The image processor 12 executes predetermined image processing, such as white balance adjustment, gamma correction and digital-to-analog conversion, and outputs the processed signal as a video signal. The video signal output from the image processor 12 is applied to a display unit (not shown), whereby an image representing the internal tissue OB is displayed on the display screen of the display unit.

As will be described below in detail, the ordinary light source 4 and excitation light source 8 are both turned off for a fixed period of time when the observation mode is changed over. The data obtained by sensing the image of the internal tissue OB by the CCD when the light sources are off is input to a dark current memory 11. The data received from the CCD 31 when both light sources are off indicates the dark current of the CCD 31 (i.e., the data is dark-current data). Though dark-current data is obtained by imaging the internal tissue over a period of time equivalent to a plurality of frames (where one frame is equivalent to 1/30 of a second), the duration of imaging may be less than one frame. The image data (image data obtained in the ordinary-light observation mode and image data obtained in the fluorescent observation mode) input to the image processor 12 is corrected using the dark-current data.

Figure 2:
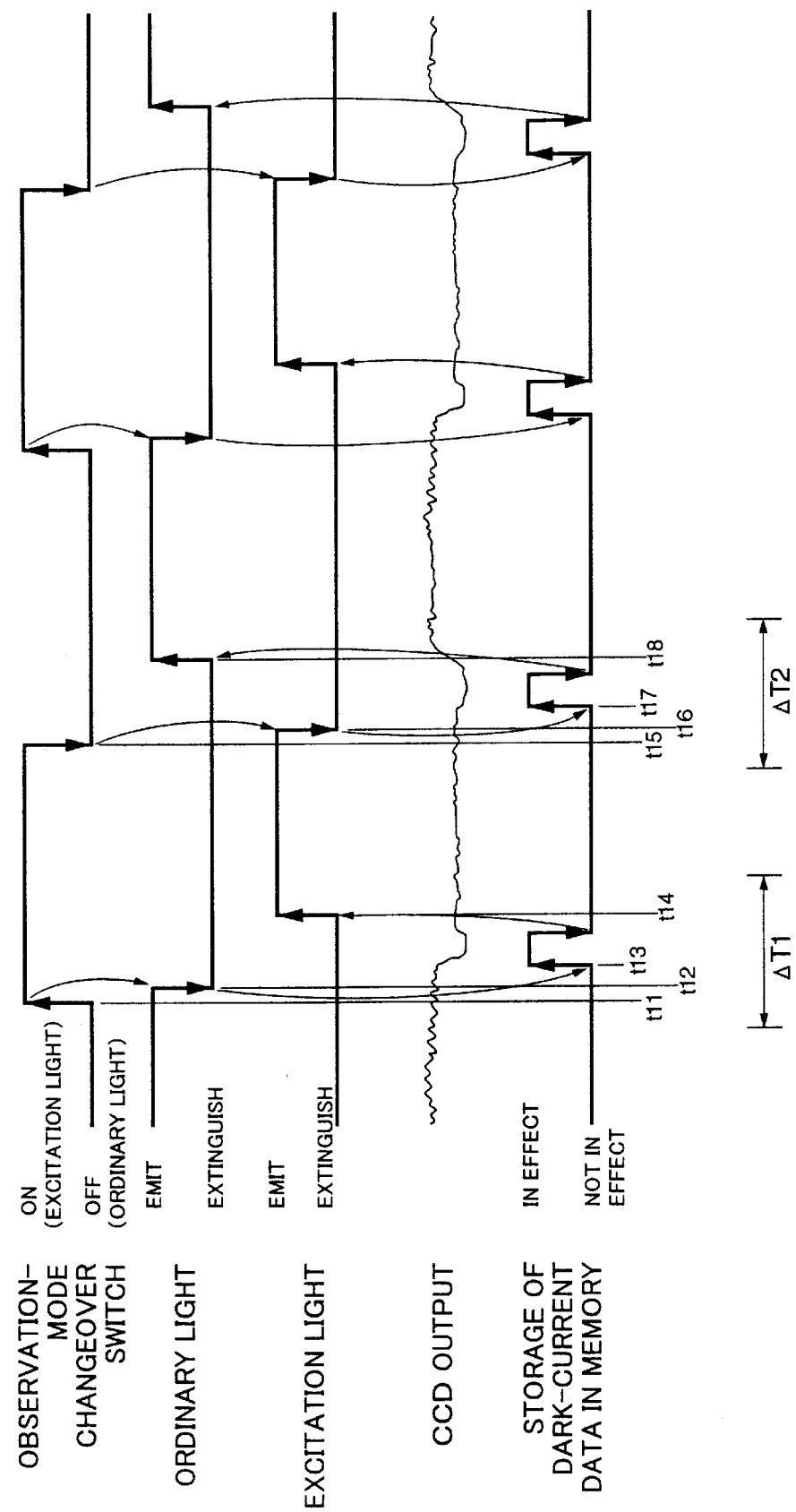
FIG. 2 is a time chart for when internal tissue is imaged using the endoscope apparatus of the first embodiment.
Figure 3:
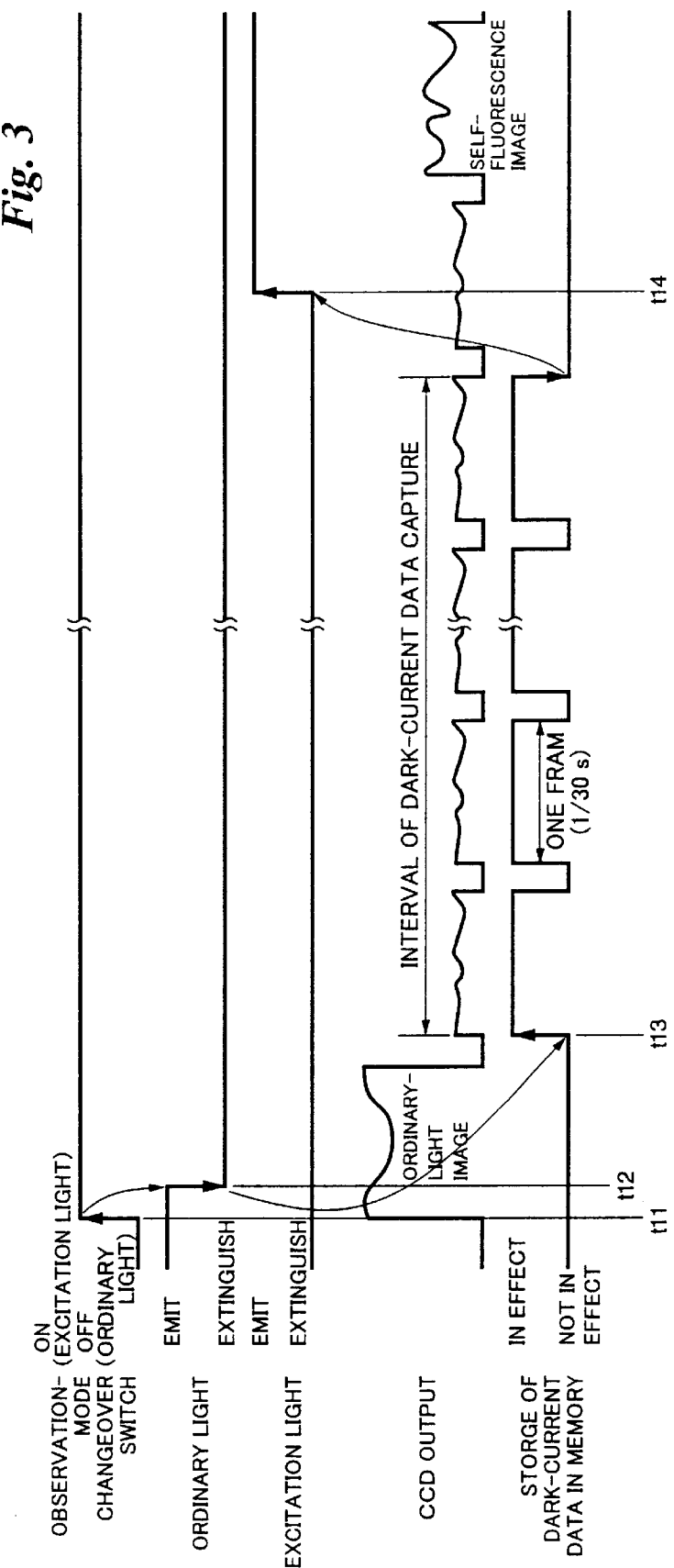
FIGS. 3 and 4 illustrate enlargements of parts of the time chart of FIG. 2.
Figure 4:
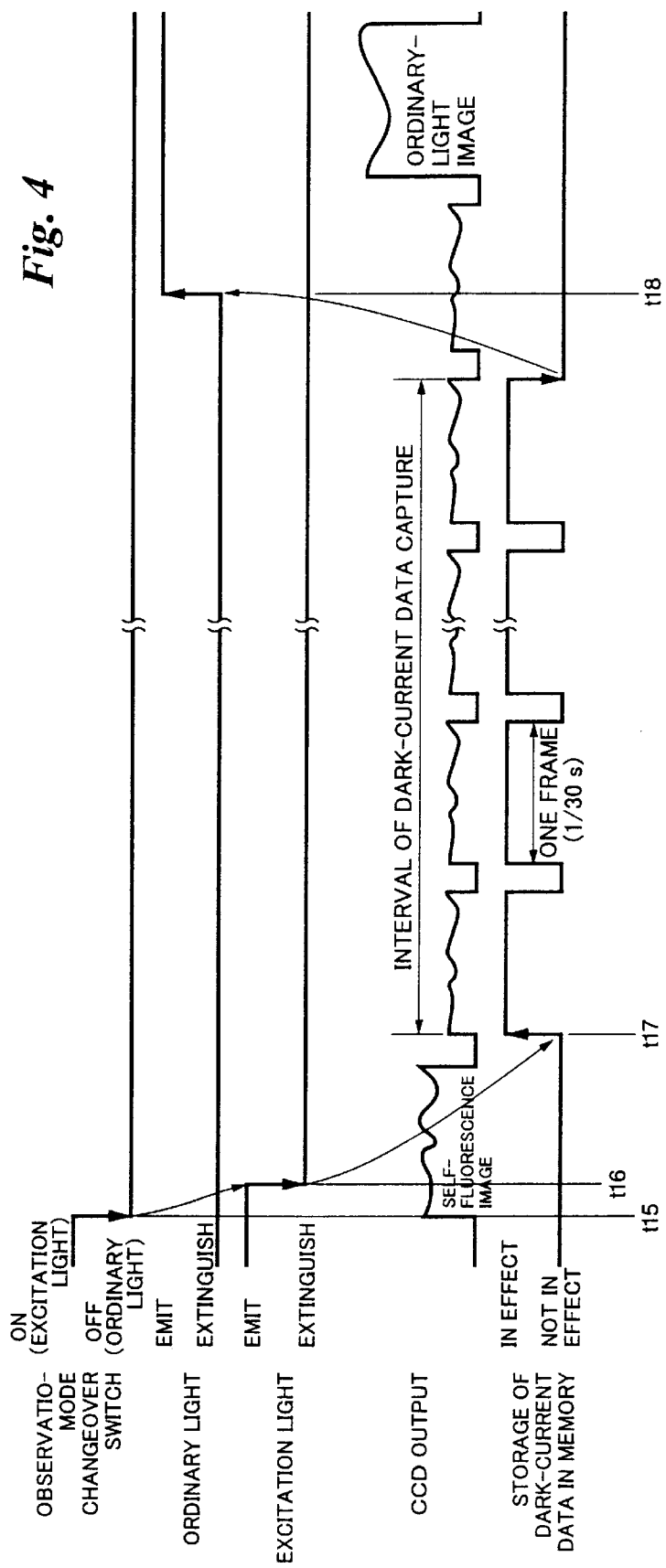

FIG. 2 is a time chart for when the internal tissue OB is imaged by the endoscope apparatus shown in FIG. 1, FIG. 3 illustrates an enlargement of time interval ΔT1 in FIG. 2, and FIG. 4 illustrates an enlargement of time interval ΔT2 in FIG. 2.

Assume that the switch circuit 2 is on, so that the ordinary light source 4 is emitting white light. If the observation-mode changeover switch 21 is turned on at time t11, the switch circuit 2 turns off at time t12, as a result of which the emission of white light from the ordinary light source 4 ceases. Even though the observation-mode changeover switch 21 has been turned on, the switch circuit 6 does not turn on immediately. When time t14 arrives following a further elapse of time, the switch circuit 6 turns on and the excitation light source 8 emits excitation light, thereby illuminating the internal tissue OB. From time t12 to time t14, therefore, the internal tissue OB is not illuminated and is in total darkness.

When time t13 within the period of total darkness arrives, the internal tissue OB is imaged by the CCD 31 and the dark-current data is applied to the dark current memory 11 (i.e., capture of dark-current data is in effect), as described above.

When the aforementioned time t14 arrives, the switch circuit 6 is turned on and the excitation light source 8 emits excitation light, thereby illuminating the internal tissue OB. The internal tissue OB produces self-fluorescence and image data representing the self-fluorescent image of the internal tissue OB is input to the image processor 12, as described earlier. Since the dark-current data from the dark current memory 11 also is being applied to the image processor 12, the dark-current data is subtracted from the entered self-fluorescent image data (i.e., a dark-current correction is applied). The self-fluorescent image data that has undergone the dark-current correction is applied to the display unit and the image of the internal tissue OB is displayed, as described earlier. The physician performs diagnosis by observing the displayed image of the internal tissue OB.

Since the dark-current correction is applied using dark-current data obtained under conditions in which the internal tissue OB is not being illuminated, the CCD 31 is shielded from light almost completely so that comparatively accurate dark-current data is obtained. Further, since the dark current is measured under conditions in which the CCD 31 is within the body of the patient, the effects of a fluctuation in dark current caused by a change in temperature can be eliminated. This makes it possible to achieve a comparatively accurate correction for dark current.

If the observation-mode changeover switch 21 is turned off at time t15, the switch circuit 6 turns off at time t16, as a result of which the emission of excitation light from the excitation light source 8 ceases. Since the ordinary light source 4 is off, both the ordinary light source 4 and excitation light source 8 are in the non-emissive state and, hence, the internal tissue OB is in total darkness. When time t17 within the period of total darkness arrives, the internal tissue OB is imaged by the CCD 31 and, as described above, the dark-current data is obtained and is stored in the dark current memory 11.

When time t18 arrives, the switch circuit 2 is turned on and the ordinary light source 4 emits ordinary light, thereby illuminating the internal tissue OB. The image of the internal tissue OB illuminated by the ordinary light is sensed and image data representing the image of the internal tissue OB is obtained. The image data representing the internal tissue OB is corrected in the image processor 12 based upon the dark-current data. Since the dark-current correction is applied also at the time of imaging under illumination with ordinary light, the obtained image of the internal tissue OB is devoid of the effects of dark current. Of course, an arrangement may be adopted in which the dark-current correction is applied only at the time of imaging under illumination with excitation light and not at the time of imaging under illumination with ordinary light. Further, it may be so arranged that when still-picture photography is possible, a shutter is turned on and the dark-current correction is applied when a still picture is taken.

Figure 5:
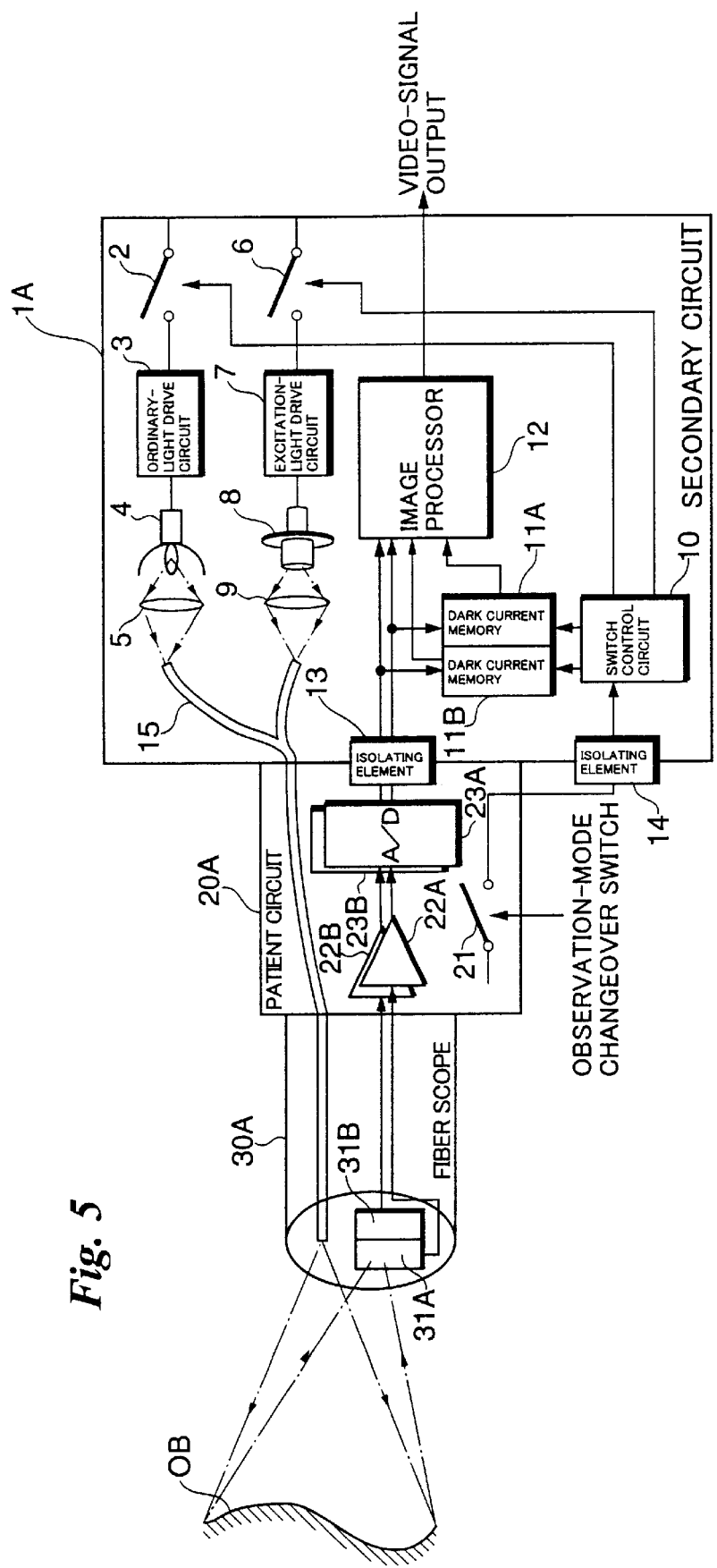
FIG. 5 is a block diagram illustrating the electrical structure of an endoscope apparatus according to a second embodiment of the present invention.

FIG. 5 is a block diagram illustrating the electrical structure of an endoscope apparatus according to a second embodiment of the present invention. Components identical with those shown in FIG. 1 are designated by like reference characters and need not be described again.

In the endoscope apparatus shown in FIG. 5, the tip of a fiber scope 30A is provided with a first CCD 31A for the ordinary-light observation mode and a second CCD 31B for an excitation-light observation mode. The internal tissue OB is imaged by the first CCD 31A when the internal tissue OB is illuminated with ordinary light and by the second CCD 31B when the internal tissue OB is illuminated with excitation light.

The video signal output from the first CCD 31A is amplified by an amplifier 22A within a patient circuit 20A. The amplified video signal is converted to digital image data in an analog/digital converter 23A, and the digital image data obtained by the conversion is input to the image processor 12. When both the ordinary light source 4 and excitation light source 8 are off, image data output from the analog/digital converter 23A is applied to and stored in a first dark current memory 11A in the manner described earlier. The stored image data is applied to the image processor 12, where it is subjected to the dark-current correction.

The video signal output from the second CCD 31B is amplified by an amplifier 22B within a patient circuit 20B. The amplified video signal is converted to digital image data in an analog/digital converter 23B, and the digital image data obtained by the conversion is input to the image processor 12. When both the ordinary light source 4 and excitation light source 8 are off, image data output from the analog/digital converter 23B is applied to and stored in a second dark current memory 11B in the manner described earlier. The stored image data is applied to the image processor 12, where it is subjected to the dark-current correction.

FIG. 6 is a time chart for when the internal tissue OB is imaged by the endoscope apparatus shown in FIG. 5.

If the observation-mode changeover switch 21 is turned on at time t21, which is when the excitation light source 8 is off, the ordinary light source 4 turns off at time t22. When time t24 arrives, the excitation light source 8 emits excitation light. From time t22 to t24, the internal tissue OB is in total darkness. When the internal tissue OB is in total darkness, the internal tissue OB is imaged by the second CCD 31B and, at time t23, the dark-current data is stored in the second dark current memory 11B, as mentioned above. The internal tissue OB is imaged by the second CCD 31B after time t24 and the image data representing the image of the internal tissue OB is input to the image processor 12. The dark-current data that has been stored in the second dark current memory 11B is subtracted from the image data, thereby applying the dark-current correction.

If the observation-mode changeover switch 21 is turned off at time t25, the excitation light source 8 is extinguished at time t26. The ordinary light source 4 emits lights when time t28 arrives. From time t26 to t28, the internal tissue OB is in total darkness. The internal tissue OB is imaged by the first CCD 31A from time t26 to t28 and the dark-current data is stored in the first dark current memory 11A, as described above, at time t27. The internal tissue OB is imaged by the first CCD 31A after time t28 and the image data representing the image of the internal tissue OB is input to the image processor 12. The dark-current data that has been stored in the first dark current memory 11A is subtracted from the image data, thereby applying the dark-current correction.

Thus, two CCDs, namely the CCD 31A employed in the ordinary-light observation mode and the CCD 31B employed in the excitation-light observation mode, can be used, and it can be so arranged that the two dark-current memories 11A and 11B are used. It goes without saying that it can be so arranged that a single dark-current memory is used even in a case where the two CCDs 31A and 31B are employed.

Further, detection of dark-current data may be performed whenever the observation mode is changed over, and an arrangement may be adopted in which use is made of dark-current data, once this data has been detected, to correct image data obtained by imaging performed subsequently. Further, the detection of dark-current data need not be performed immediately before the acquisition of image data that is corrected using the dark-current data.

As many apparently widely different embodiments of the present invention can be made without departing from the spirit and scope thereof, it is to be understood that the invention is not limited to the specific embodiments thereof except as defined in the appended claims.

What is claimed is:

1. An endoscope apparatus comprising:
   a light source for emitting first light having a first wavelength characteristic in a first observation mode and emitting second light having a second wavelength characteristic in a second observation mode;
   an image sensing device for outputting image data representing an object of interest in an area illuminated by light emitted from said light source;
   a controller for controlling said light source so as to halt emission of light when there is a mode changeover between the first and second observation modes; and
   a correction device for correcting image data, which is output from said image sensing device and represents the image of the object of interest that was illuminated by at least one of the first light and second light, after the emission of light is halted, using data output from said image sensing device when the emission of light from the light source is halted by said controller.

2. The apparatus according to claim 1, wherein the image data that is corrected by said correction device is image data of an object of interest that was illuminated by said light source immediately after halting of the emission of light.

3. The apparatus according to claim 1, wherein said controller controls said light source so as to halt the emission of light every time there is a mode changeover between the first and second observation modes; and
   said correction device corrects the image data, which is output from said image sensing device and represents the image of the object of interest that was illuminated by at least one of the first light and second light, immediately after the emission of light is halted every time the emission of light is halted, using image data output from said image sensing device and representing the image of the subject every time the emission of light from said light source is halted by said controller.

4. The apparatus according to claim 1, wherein the first light of said light source is visible light and the second light of said light source is excitation light for obtaining a fluorescent image of internal tissue.

5. A method of controlling an endoscope apparatus having a light source for emitting first light having a first wavelength characteristic in a first observation mode and emitting second light having a second wavelength characteristic in a second observation mode, and an image sensing device for outputting image data representing an object of interest in an area illuminated by light emitted from the light source, said method comprising the steps of:
   controlling the light source so as to halt emission of light when there is a mode changeover between the first and second observation modes; and
   correcting image data, which is output from the image sensing device and represents the image of the object of interest that was illuminated by at least one of the first light and second light, after the emission of light is halted, using data output from the image sensing device when the emission of light from the light source is halted.

* * * * *